United States Patent
Tuschel et al.

(10) Patent No.: US 7,408,636 B2
(45) Date of Patent: Aug. 5, 2008

(54) METHOD AND APPARATUS FOR DARK FIELD CHEMICAL IMAGING

(75) Inventors: David Tuschel, Monroeville, PA (US); Wesley H. Hutchison, Bridgeville, PA (US); Myles P. Berkman, Pittsburgh, PA (US)

(73) Assignee: ChemImage Corporation, Pittsburgh, PA (US)

( * ) Notice: Subject to any disclaimer, the term of this patent is extended or adjusted under 35 U.S.C. 154(b) by 354 days.

(21) Appl. No.: 10/879,636

(22) Filed: Jun. 30, 2004

(65) Prior Publication Data

US 2006/0001869 A1   Jan. 5, 2006

Related U.S. Application Data

(63) Continuation-in-part of application No. 10/698,243, filed on Oct. 31, 2003, which is a continuation-in-part of application No. 10/698,584, filed on Oct. 31, 2003.

(60) Provisional application No. 60/422,604, filed on Oct. 31, 2002.

(51) Int. Cl.
  *G01J 3/44* (2006.01)
(52) U.S. Cl. ........................ 356/301; 356/417
(58) Field of Classification Search ............ 356/301
  See application file for complete search history.

(56) References Cited

U.S. PATENT DOCUMENTS

| | | | |
|---|---|---|---|
| 3,641,344 A * | 2/1972 | Markle | ........................ 356/307 |
| 4,030,827 A * | 6/1977 | Delhaye et al. | ............. 356/301 |
| 4,660,151 A | 4/1987 | Chipman et al. | |
| 4,701,838 A | 10/1987 | Swinkels et al. | |
| 4,766,551 A | 8/1988 | Begley | |
| 4,885,697 A | 12/1989 | Hubner | |
| 5,072,338 A | 12/1991 | Hug et al. | |
| 5,121,337 A | 6/1992 | Brown | |
| 5,121,338 A | 6/1992 | Lodder | |
| 5,124,932 A | 6/1992 | Lodder | |
| 5,311,445 A | 5/1994 | White | |
| 5,324,567 A | 6/1994 | Bratchley et al. | |
| 5,481,476 A | 1/1996 | Windig | |
| 5,606,164 A | 2/1997 | Price et al. | |
| 5,610,836 A | 3/1997 | Alsmeyer et al. | |
| 5,623,932 A * | 4/1997 | Ramanujam et al. | ........ 600/317 |
| 5,710,713 A | 1/1998 | Wright et al. | |
| 5,751,415 A | 5/1998 | Smith et al. | |
| 5,822,219 A | 10/1998 | Chen et al. | |

(Continued)

OTHER PUBLICATIONS

Conti, S., et al., "Traces of Polymethylsiloxane in case histories of rape: technique for detection," Elsvier Science Ireland Ltd, Forensic Science International, Jan. 1995, pp. 121-128.

(Continued)

*Primary Examiner*—Kara E Geisel
(74) *Attorney, Agent, or Firm*—Duane Morris LLP

(57) ABSTRACT

The disclosure is generally directed to a method and apparatus for providing an image of a sample. The apparatus includes an illuminating source for transmitting photons to a sample. The transmitted photons illuminate the sample or are scattered upon reaching the sample. A lens collects the scattered photons and transmits the scattered photons to a tunable filter for forming an image. The illuminating photons traveling from the illuminating source to the sample do not pass through the lens.

69 Claims, 3 Drawing Sheets

U.S. PATENT DOCUMENTS

| | | | |
|---|---|---|---|
| 5,866,430 A * | 2/1999 | Grow | 436/172 |
| 6,002,476 A | 12/1999 | Treado | |
| 6,008,888 A | 12/1999 | Nottke et al. | |
| 6,124,926 A * | 9/2000 | Ogawa et al. | 356/318 |
| 6,239,904 B1 | 5/2001 | Serfling et al. | |
| 6,485,413 B1 * | 11/2002 | Boppart et al. | 600/160 |
| 6,485,981 B1 | 11/2002 | Fernandez | |
| 6,549,861 B1 | 4/2003 | Mark et al. | |
| 6,584,413 B1 | 6/2003 | Keenan et al. | |
| 6,765,668 B2 * | 7/2004 | Gardner et al. | 356/301 |
| 6,847,447 B2 * | 1/2005 | Ozanich | 356/326 |
| 2001/0052979 A1 | 12/2001 | Treado et al. | |
| 2002/0016533 A1 | 2/2002 | Marchitto et al. | |
| 2002/0065468 A1 * | 5/2002 | Utzinger et al. | 356/327 |
| 2004/0021860 A1 | 2/2004 | Gardner, Jr. et al. | |
| 2006/0158645 A1 * | 7/2006 | Maier et al. | 356/301 |
| 2007/0070343 A1 * | 3/2007 | Cohen et al. | 356/301 |

OTHER PUBLICATIONS

Lee, G.S.H., et al., "A Methodology Based on NMR Spectroscopy of the Forensic Analysis of Condoms," St. Andrews Centre for Advanced Materials, pp. 808-821, undated.

Maynard, P., et al., "A protocol for the forensic analysis of condom and personal lubricants found in sexual assault cases," Forensic Science International, 124 (2001), pp. 140-156.

Roux, C., et al., "Evaluation of 1,2-Indanedione and 5,6-Dimethoxy-1,2-Indanedione for the Detection of Latent Fingerprints on Porous Surfaces," Journal of Forensic Sciences, vol. 45(4), 2000, pp. 761-769.

Roux, C., et al., "A study to investigate the evidential value of blue and black ballpoint pen inks in Australia," Forensic Science International, 101 (1999), pp. 167-176.

Mazzella, W.D., et al., "Classification and Identification of Photocopying Toners by Diffuse Reflectance Infrared Fourier Transform Spectroscopy (DRIFTS): I. Preliminary Results," Journal of Forensic Sciences, JFSCA, vol. 36, No. 2, Mar. 1991, pp. 449-465.

Mazzella, W.D., et al., "Classification and Identification of Photocopying Toners by Diffuse Reflectance Infrared Fourier Transform Spectroscopy (DRIFTS): II. Final Report," Journal of Forensic Sciences, JFSCA, vol. 36, No. 3, May 1991, pp. 820-837.

Brunelle, R.L., "Questioned Document Examination," Bureau of Alcohol, Tobacco, and Firearms, U.S. Treasury Department, 1982.

Robertson, J., et al., "The Persistence of Textile Fibres Transferred During Simulated Contacts," Journal of Forensic Sciences, vol. 22, No. 4, Oct. 1982, p. 353-360.

Gaudette, B.D., "The Forensic Aspects of Textile Fiber Examination," Central Forensic Laboratory, Royal Canadian Mounted Police, undated.

Pounds, C.A., et al., "The Transfer of Fibres between Clothing Materials During Simulated Contacts and their Persistence During Wear: Part I—Fibre Transference," Journal of Forensic Sciences, vol. 15, 1975, pp. 17-27.

Pounds, C.A., et al., "The Transfer of Fibres between Clothing Materials During Simulated Contacts and their Persistence During Wear: Part II—Fibre Persistence," Journal of Forensic Sciences, vol. 15, 1975, pp. 29-37.

Maynard, P., et al., "Adhesive Tape Analysis: Establishing the Evidential Value of Specific Techniques," Journal of Forensic Sciences, vol. 46(2), 2001, pp. 280-287.

Caetano, M.R., et al., "Evaluation of the importance of non-linear spectral mixing in coniferous forests," EUROPTO Conference on Remote Sensing for Agriculture, Ecosystems, and Hydrology, Barcelona, Spain, Sep. 1998.

Rasmussen, G.T., et al., "Library Retrieval of Infrared Spectra Based on Detailed Intensity Information," Applied Spectroscopy, vol. 33, No. 4, 1979.

Guilment, J., et al., "Infrared Chemical Micro-Imaging Assisted by Interactive Self-Modeling Multivariate Analysis," Applied Spectroscopy, vol. 48, No. 3, 1994.

* cited by examiner

METHOD AND APPARATUS FOR DARK FIELD CHEMICAL IMAGING

RELATED APPLICATIONS

The instant disclosure claims the filing-date benefit of application Ser. Nos. 10/698,243 and 10/698,584 filed Oct. 31, 2003 and is a continuation in part of these applications, as well as provisional application No. 60/422,604 filed Oct. 31, 2002, each of which is incorporated herein by reference in its entirety. In addition cross-reference is made to U.S. application Ser. No. 10/882,082 (now U.S. Pat. No. 7,046,359 B2) filed concurrently herewith and entitled "System and Method for Dynamic Chemical Imaging" which is also incorporated herein in its entirety.

BACKGROUND

Conventional spectroscopic imaging systems are generally based on the application of high resolution, low aberration, lenses and systems that produce images suitable for visual resolution by a human eye. These imaging systems include both microscopic spectral imaging systems as well as macroscopic imaging systems and use complex multi-element lenses designed for visual microscopy with high resolution aberrations optimized for each desired magnification. However, transmitting illumination through such complex lenses attenuates the incident beam and creates spurious scattered light.

Further, each lens magnification results in a particular collection angle for the scattered light. Generally, at lower magnification the collection efficiency is strongly reduced as the focal distance increases. Consequently, the lens must be placed further away from the sample. For macro-systems (i.e., systems needing a broader view of the larger sample rather than a high magnification of a smaller portion of the sample), the reduced collection aperture severely limits the collected signal. The need for high collection efficiency may be critical for spectroscopic imaging at all distances.

Much of the optical signal detected in the conventional systems is dramatically reduced because of the system configuration and the need to maintain high resolution by removing optical aberrations. Conventional systems have been largely conceived based on the premises and the requirements of optical microscopy. Namely, the need to present a high resolution, zero-aberration, image to the operator who uses visual inspection to perceive the image. In addition, conventional micro-Raman systems achieve their high spatial resolution through the focus of the laser beam to a diffraction-limited spot by the microscope's objective lens. These design premises and system configurations limit the light delivery in conjunction with the collection efficiency of the spectroscopic imaging system.

Finally, design premises based on resolution and throughput requirements for spectral imaging have not been changed as components have been adopted or selected from commercial optical systems. Illumination through such optical systems produces attenuation (reduced signal) and internal scattering (higher background noise) which are detrimental to the system's performance. Thus, there is a need for a low cost, high throughput and efficient chemical imaging system.

SUMMARY OF THE DISCLOSURE

In one embodiment, the disclosure relates to an apparatus for forming an image of a sample. The apparatus includes a photon transmitter for transmitting a plurality of photons to the sample. Each of the plurality of the transmitted photons either scatter upon reaching the sample or can be absorbed by the sample causing subsequent emission (luminescence) at different wavelengths. The scattered photons may be Raman scattered photons. The scattered photons or the emitted photons are collected by a lens and directed to a filter for forming an image of the sample. The filter may include one or more photonic crystals, a mirror, a solid state optical device and a micromachined tunable filter. The image can be a Raman image, i.e., an image formed from Raman scattered photons. The photon transmitter, the sample and the filter are positioned relative to each other so as to form an oblique angle.

In another embodiment, the disclosure relates to a device for forming one or more wavelength-resolved images of a sample. The images can include Raman and/or luminescence (emitted light) images. The device includes a photon emission source transmitting photons to illuminate a sample. The photons reaching the sample may be absorbed by the sample or scatter. An optical lens may be placed proximal to the sample for collecting the scattered photons. The collected scattered photons are then directed to an electro-optical filter for forming a wavelength-resolved image of the sample. The filter may be a liquid crystal tunable filter and a laser optical filter may be interposed between the optical lens and the tunable filter.

In a method according to one embodiment of the disclosure, a spatially accurate wavelength-resolved image of a sample is obtained by illuminating a sample with a plurality of photons. The photons are either absorbed by the sample or scatter upon reaching the sample. Next, the scattered or emitted photons are collected by an optical device and directed to a tunable filter for image processing. Collecting the scattered photons can include collecting scattered photons having a wavelength in a predetermined wavelength band. Further, collecting the scattered photons can occur during a predetermined time interval. It has been found that by collecting the scattered photons through an optical device and not allowing the illuminating photons to pass through the same optical device an image of the sample can be obtained. The wavelength-resolved image includes a Raman image.

A spatially accurate wavelength-resolved image is an image of a sample that is formed from multiple "frames" wherein each frame has plural spatial dimensions and is created from photons of a particular wavelength (or wave number) or from photons in a particular wavelength band (or wave number band) so that the frames may be combined to form a complete image across all wavelengths (wave numbers) of interest.

In still another method according to an embodiment of the disclosure, a method for obtaining a spatially accurate wavelength-resolved image of a sample is disclosed. The method includes illuminating a sample with a plurality of photons where upon reaching the sample, the photons either are absorbed by the sample or scatter. The scattered photons may then be collected by an optical device and forwarded for further image processing. The emitted photons (luminescence) may then be collected by an optical device and forwarded for further image processing. The illuminating photons are substantially ignored by the optical device.

DETAILED DESCRIPTION OF THE DISCLOSURE

The various embodiments of the disclosure provide low cost optical device and methods particularly suited for spectral imaging systems by providing higher light delivery in conjunction with high collection efficiency and reduced scattering of the resolutions of imaging applications. Conventional lens objectives are more complex and costly than the apparatus disclosed according to the principles disclosed herein. Since the color and the resolution of the viewed sample is determined by the tunable filter and the resolution of the imaging detector, the system need not use a conventional high resolution, low aberration lens as used in conventional microscopes. Indeed, a simpler reduced resolution/aberration lens can be designed with larger numeral aperture to increase system throughput (light delivery and collection efficiency) while providing the same quality resolution as the conventional systems.

The radiation used to illuminate the sample need not pass through the optical train of a conventional microscope or macroscope. It can be illuminated from the underside of the sample. This results in reduced internal scattering and attenuation of the incident exciting photons. The location of the illumination source external to the optical train further enables a simpler, low power/low cost illumination sources as well as a lower cost of integration of several illumination sources into one system.

In micro-Raman spectroscopy, for example, the illuminating beam and the microscope are focused on a diffraction-limited spot for collecting the Raman scattered light. The same imaging system is also used in full field-of-view Raman imaging. Such instrument configuration has proved optically inefficient and costly. The combined optical losses due to laser light delivery and Raman scattered light collection can severely limit the number of Raman chemical imaging applications. Optical inefficiency occurs because much of the optical signal of interest must be spectrally separated from the incident laser light as the latter is many orders of magnitude more intense than the Raman scattered light. Consequently, the detected Raman signal is dramatically reduced because it must be spectrally and angularly resolved.

Figure 1:
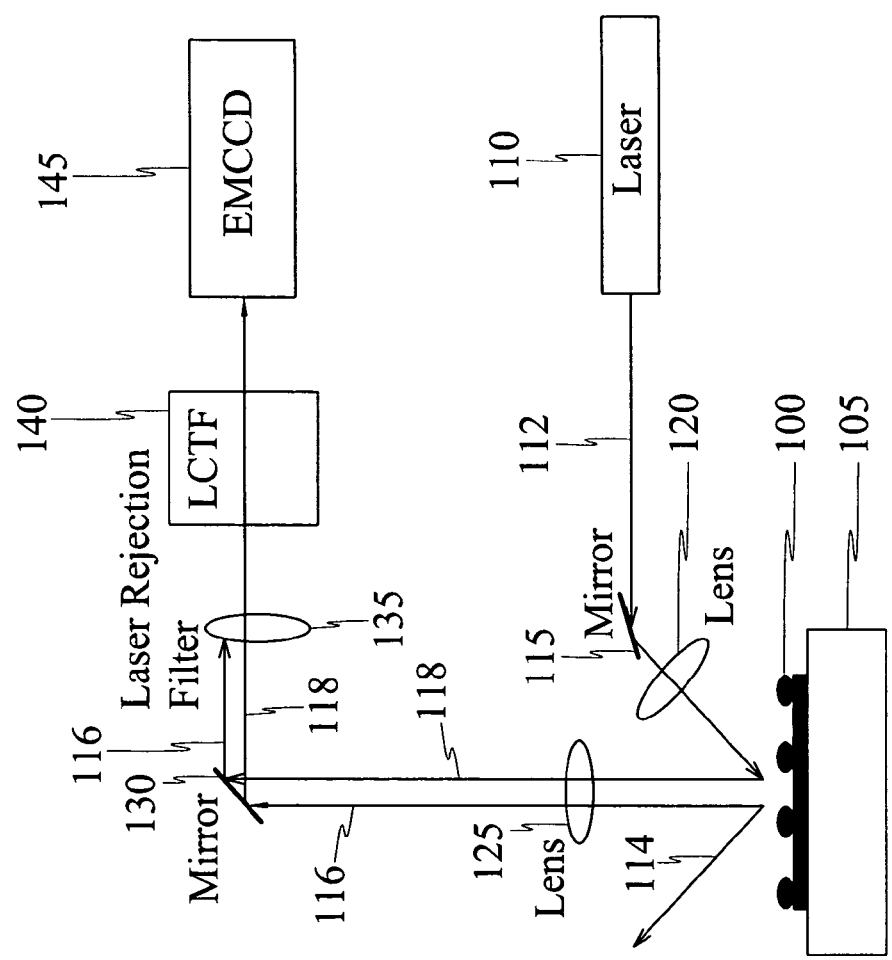
FIG. 1 schematically represents an apparatus according to one embodiment of the disclosure.

FIG. 1 schematically represents an apparatus according to one embodiment of the disclosure. The apparatus of FIG. 1 enables providing a high optical throughput for imaging low light levels at variable magnification. Referring to FIG. 1, sample 100 is positioned on substrate 105. Substrate 105 can be any conventional microscopic slide or other means for receiving and optionally securing sample 100.

Light source 110 is positioned to provide incident light to sample 100. Light source 110 can include any conventional photon source, including laser, LED, and other IR or near IR devices. Light source 110 may also be selected to provide evanescence illumination of the sample. In one embodiment, the wavelength of the source is in the range of about 15-25 $cm^{-1}$. Referring to FIG. 1, it should be noted that light source 110 is positioned to provide incident light at an angle to sample 100 as opposed to light shining orthogonal to sample 100. In other words, the radiation used to illuminate the sample need not pass through the optical train of a conventional microscope (or macroscope); rather, it can illuminate the sample at an oblique angle from above or below sample 100. Photon beam 112 is received and deflected by mirror 115 through lens 120. Lens 120 may optionally be used to focus the light on sample 100. Alternatively, the photon beam 112 may be directed towards the sample 100 without the need for the mirror 115.

The multitude of photons in beam 112 reaching sample 100 are absorbed by the sample or scatter upon reaching the sample. Scattered photons are schematically represented as beams 116 and 118 while spectrally reflected photons are represented schematically as beam 114. Luminescence emitted photons are also represented as beam 118. Optical lens 125 is positioned to receive emitted and scattered photon beams 116 and 118. The term 'luminescence' has been conventionally used to include a wide range of optical processes including fluorescence, phosoporescence, photoluminescence, electroluminescence, chemiluminescence, sonoluminescence, thermoluminescence and even upconversion. Optical lens 125 may be used for gathering and focusing received photon beams. This includes gathering and focusing both polarized and the un-polarized photons. In general, the sample size determines the choice of light gathering optical lens 125. For example, a microscope lens may be employed for analysis of the sub-micron to micrometer specimens. For larger samples, macro lenses can be used. Optical lens 125 (as well as lens 120) may include simple reduced resolution/aberration lens with larger numerical aperture to thereby increase system's optical throughput and efficiency.

Mirror 130 is positioned to direct emitted or scattered photon beams 118 to tunable filter 140. It should be noted that placement of mirror 130 is optional and may be unnecessary in configurations where tunable filter is positioned above sample 100.

Laser rejection filter 135 may be positioned prior to tunable filter 140 to filter out scattered illumination light represented by beam 116 and to optimize the performance of the system. The laser rejection filter 135 can be a notch filter. In other words, rejection filter 135 enables spectral filtering of light at the illuminating wavelength. For optimal performance, a computer may be used to control any of the optical devices shown in FIG. 1 including the lenses (120, 125, 135), mirrors (115, 130) and the tunable filter 140.

A conventional tunable filter (including electro-optical tunable filters) including liquid crystal tunable filter ("LCTF") or acousto-optical tunable filter ("AOTF") can be used to further the principles of the disclosure. The electro-optical filters (interchangeably, tunable filters) allow specific wavelengths or ranges of wavelengths of light to pass through as an image, depending on the control signals placed on the device by a controller (not shown). The wavelengths that can be passed through tunable filter 140 may range from 200 nm (ultraviolet) to 2000 nm (i.e., the far infrared). The choice of wavelength depends on the desired optical region and/or the nature of the sample being analyzed.

Image sensor 145 may be a digital device such as a two-dimensional, image focal plane array ("FPA"). The optical region employed to characterize the sample of interest governs the choice of FPA detector. For example, silicon charge-coupled device ("CCD") detectors, can be employed with visible wavelength fluorescence and Raman spectroscopic imaging, while gallium arsenide (GaAs) and gallium indium arsenide (GaInAs) FPA detectors can be employed for image analyses at near infrared wavelengths. The choice of such devices depends on the type of sample being analyzed. Image sensor 145 produces digital images of the entire view of the sample as processed by tunable filter 140.

Figure 2:
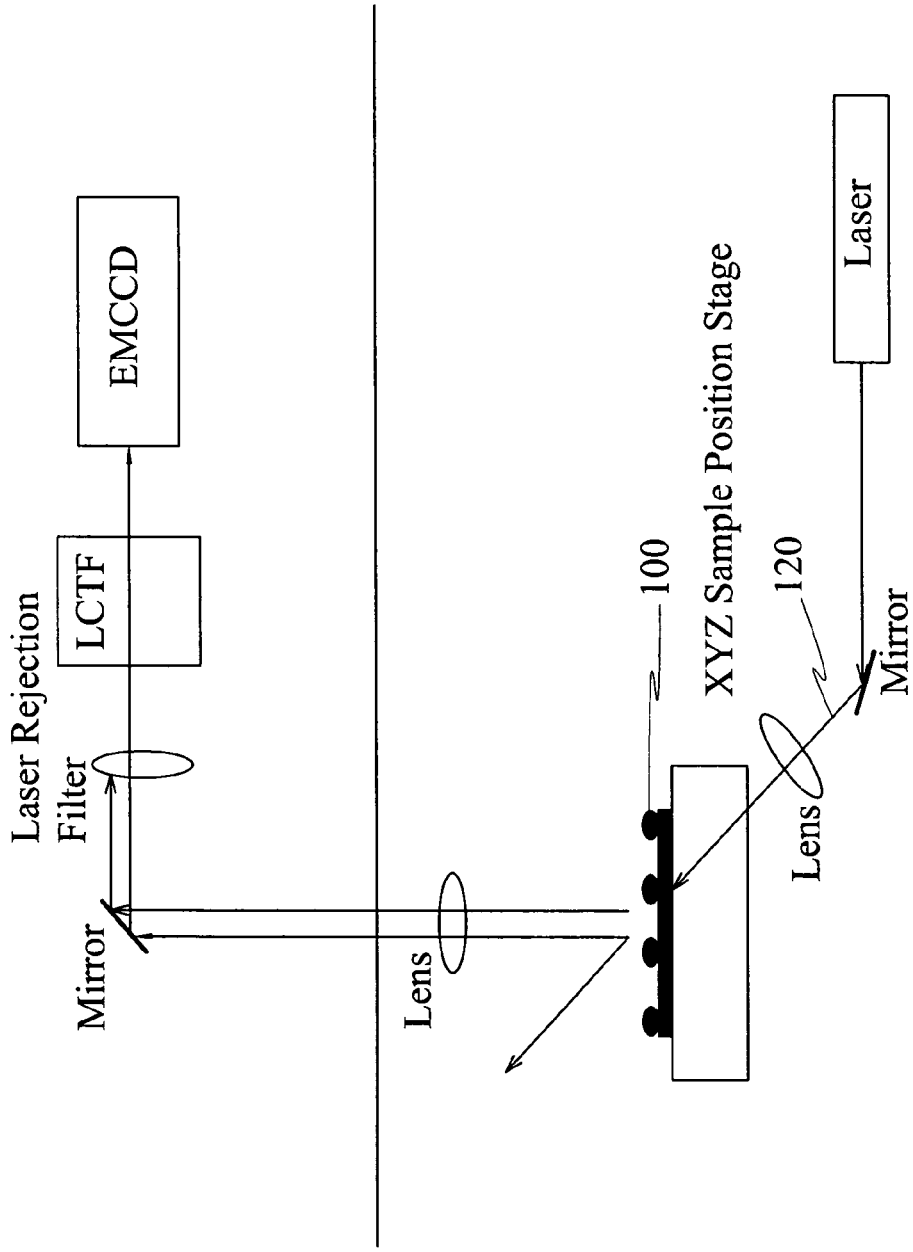
FIG. 2 schematically represent an apparatus according to another embodiment of the disclosure.

FIG. 2 schematically represents an apparatus according to another embodiment of the disclosure. More specifically, FIG. 2 schematically shows a high optical throughput configuration for imaging low light levels at variable magnification. The collection optics are similar to that illustrated in FIG. 1 but with illumination from the underside of sample 100.

It is noted that in both FIGS. 1 and 2, sample 100 is illuminated at an oblique angle. Specifically referring to FIG. 2, photonic beam 120 and the plane axis of sample 100 define an oblique angle. It has been found that through oblique illumination, a so-called "Dark Field Raman Imaging" is developed. As opposed to the conventional bright field Raman configuration, the dark field Raman imaging decouples the image capture optics from the deliver of exciting radiation. Consequently, internal scattering and attenuation of the incident radiation has been minimized. Also, the location of the optical source external to the optical train further enables a simpler, less expensive integration of several illumination sources into the system. The application of this configuration is not limited to Raman and luminescence imaging and can be successfully used, for example, with conventional spectroscopy.

The configuration disclosed herein is particularly suitable for Raman imaging of micro fluid circuits or biological samples undergoing change. These changes may include displacement, chemical interaction, a change in chemical state, phase change, growth, shrinkage, chemical decomposition, chemical metabolization and physical strain.

Figure 3:
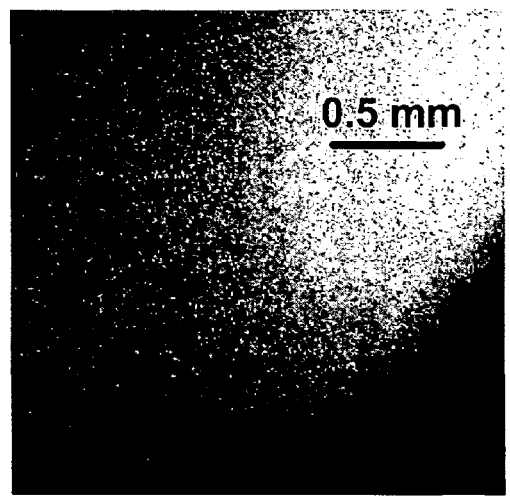
FIG. 3 shows Raman image of a sample using a method and apparatus in accordance with one embodiment of the disclosure.
Figure 4:
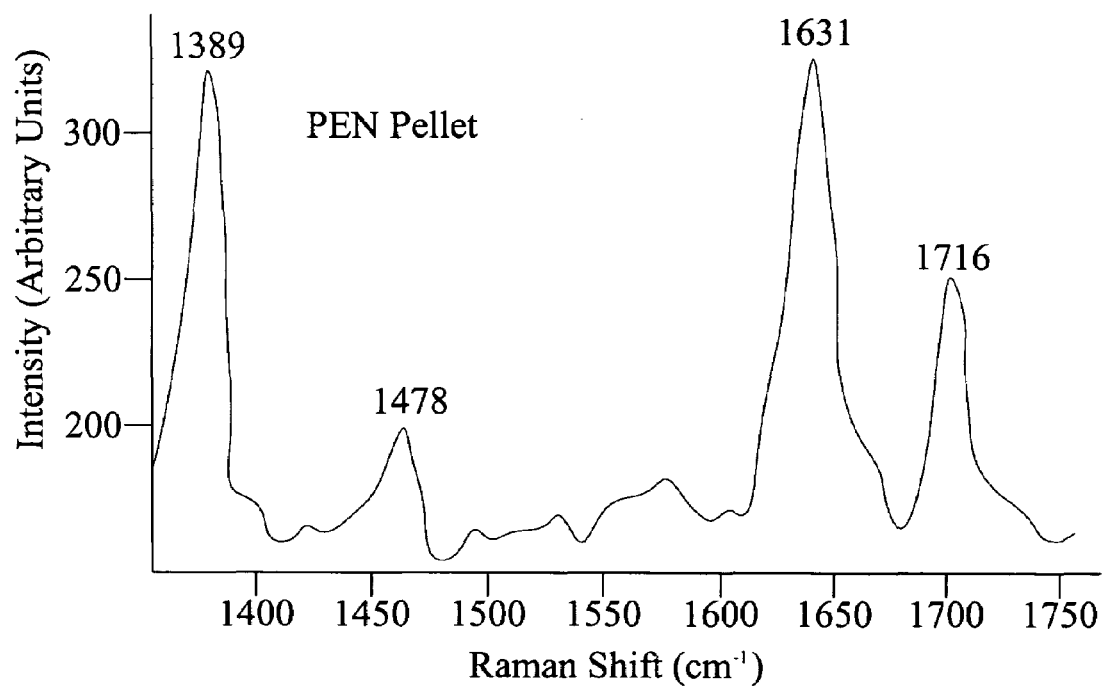
FIG. 4 shows a Raman spectrum extracted from the hyperspectral image of polyethylene naphthalate shown in FIG. 4.

FIG. 3 shows Raman image of a sample using a method and apparatus in accordance with one embodiment of the disclosure. More specifically, FIG. 3 shows Raman image of a polyethylene naphthalate pellet at 1389 cm$^{-1}$ obtained with single lens imaging apparatus according to an embodiment of the disclosure. The incident power was about 100 mW of 532 nm light illuminated over a circular region 3 mm in diameter. The image was captured using a 512×512 CCD integrated for 2.0 Sec with 2×2 binning. FIG. 4 shows a Raman spectrum extracted from the hyperspectral image of polyethylene napthalate shown in FIG. 4. The Raman spectrum shown in FIG. 4 is substantially free from optical noise prevalent when using a conventional testing configuration.

Although the principles disclosed herein have been described in relation with the non-exclusive exemplary embodiments provided herein, it should be noted that the principles of the disclosure are not limited thereto and include permutations and variations not specifically described.

What is claimed is:

1. A method for obtaining a spatially accurate wavelength-resolved image of a sample, the method comprising the steps of:
    illuminating the sample with a plurality of photons to thereby produce photons scattered by the sample; and
    collecting the scattered photons through an optical device to thereby obtain a spatially accurate wavelength-resolved image of the sample,
    wherein the illuminating photons do not pass through the optical device,
    wherein the step of collecting the scattered photons includes obtaining plural sets of scattered photons,
    wherein each set of scattered photons contains photons in a predetermined wavelength band different from the predetermined wavelength band of the other sets of scattered photons, and
    wherein a spatially accurate wavelength-resolved image of the sample is obtained from each set of scattered photons.

2. The method of claim 1 wherein the scattered photons include photons emitted by the sample.

3. The method of claim 1 wherein the wavelength-resolved image includes a Raman image.

4. The method of claim 1 wherein the wavelength-resolved image includes a luminescence emission image.

5. The method of claim 1 wherein the step of collecting the scattered photons occurs during a predetermined time interval.

6. The method of claim 5 wherein during said time interval the sample undergoes a change selected from the group of changes consisting of: spatial displacement, chemical interaction, chemical state, phase, growth, shrinkage, chemical decomposition, chemical metabolization, and physical strain.

7. The method of claim 1 wherein the step of illuminating the sample includes illuminating the sample with photons that travel at an angle that is oblique to a plane along which the sample is substantially oriented.

8. The method of claim 1 wherein the wavelength of the scattered photons is different than the wavelength of the illuminating photons.

9. The method of claim 1 wherein the step of illuminating the sample includes illuminating a side of the sample opposite the optical device.

10. The method of claim 1 wherein the step of illuminating the sample includes photons from an evanescent light source.

11. The method of claim 1 wherein the step of collecting scattered photons includes collecting scattered polarized photons.

12. The method of claim 1 wherein the step of collecting scattered photons includes collecting scattered un-polarized photons.

13. The method of claim 1 further comprising the step of filtering the collected photons though an optical filter.

14. The method of claim 1 further comprising the step of spectrally separating the collected photons.

15. A system for obtaining a spatially accurate wavelength-resolved image of a sample, comprising:
    a photon emission source for illuminating the sample with a plurality of photons to thereby produce photons scattered by the sample;
    an optical lens for collecting the scattered photons;
    a filter for receiving the collected scattered photons and providing therefrom filtered photons; and
    a charged couple device for receiving the filtered photons and obtaining therefrom a spatially accurate wavelength-resolved image of the sample,
    wherein the illuminating photons do not pass through the optical lens,
    wherein the scattered photons include plural sets of scattered photons,
    wherein each set of scattered photons contains photons in a predetermined wavelength band different from the predetermined wavelength band of the other sets of scattered photons, and
    wherein a spatially accurate wavelength-resolved image of the sample is obtained from each set of scattered photons.

16. The system of claim 15 wherein the scattered photons include photons emitted by the sample.

17. The system of claim 15 wherein the wavelength-resolved image includes a Raman image.

18. The system of claim 15 wherein the wavelength-resolved image includes a luminescence emission image.

19. The system of claim 15 wherein the optical lens collects the scattered photons during a predetermined time interval.

20. The system of claim 19 wherein during said time interval the sample undergoes a change selected from the group of changes consisting of: spatial displacement, chemical interaction, chemical state, phase, growth, shrinkage, chemical decomposition, chemical metabolization, and physical strain.

21. The system of claim 15 wherein the photon emission source illuminates the sample with photons that travel at an angle that is oblique to a plane along which the sample is substantially oriented.

22. The system of claim 15 wherein the wavelength of the scattered photons is different than the wavelength of the illuminating photons.

23. The system of claim 15 wherein the photon emission source illuminates a side of the sample opposite the optical device.

24. The system of claim 15 wherein the photon emission source is an evanescent light source.

25. The system of claim 15 wherein the optical lens collects scattered polarized photons.

26. The system of claim 15 wherein the optical lens collects scattered un-polarized photons.

27. The system of claim 15 further comprising an optical filter.

28. The system of claim 15 wherein the filter spectrally separates the collected photons.

29. The system of claim 15 wherein the filter includes one or more of a photonic crystal, a mirror, a solid state optical device and a micromachined tunable filter.

30. The system of claim 15 wherein the filter is a tunable filter.

31. The system of claim 30 wherein the tunable filter is an optical filter.

32. The system of claim 15 further comprising a notch filter interposed between the optical lens and the ifiter.

33. The system of claim 15 wherein the photon illumination source is positioned at an angle with respect to an axis formed by the sample and the filter.

34. A method for obtaining a spatially accurate wavelength-resolved image of a sample, the method comprising the steps of:
    illuminating the sample with a plurality of photons to thereby produce photons emitted by the sample; and
    collecting the emitted photons through an optical device to thereby obtain a spatially accurate wavelength-resolved image of the sample,
    wherein the illuminating photons do not pass through the optical device, and
    wherein the step of collecting the emitted photons includes obtaining plural sets of emitted photons,
    wherein each set of emitted photons contains photons in a predetermined wavelength band different from the predetermined wavelength band of the other sets of emitted photons, and
    wherein a spatially accurate wavelength-resolved image of the sample is obtained from each set of emitted photons.

35. The method of claim 34 wherein the wavelength-resolved image includes a Raman image.

36. The method of claim 34 wherein the wavelength-resolved image includes a luminescence emission image.

37. The method of claim 34 wherein the step of collecting the emitted photons occurs during a predetermined time interval.

38. The method of claim 37 wherein during said time interval the sample undergoes a change selected from the group of changes consisting of: spatial displacement, chemical interaction, chemical state, phase, growth, shrinkage, chemical decomposition, chemical metabolization, and physical strain.

39. The method of claim 34 wherein the step of illuminating the sample includes illuminating the sample with photons that travel at an angle that is oblique to a plane along which the sample is substantially oriented.

40. The method of claim 34 wherein the wavelength of the emitted photons is different than the wavelength of the illuminating photons.

41. The method of claim 34 wherein the step of illuminating the sample includes illuminating a side of the sample opposite the optical device.

42. The method of claim 34 wherein the step of illuminating the sample includes photons from an evanescence light source.

43. The method of claim 34 wherein the step of collecting emitted photons includes collecting emitted polarized photons.

44. The method of claim 34 wherein the step of collecting emitted photons includes collecting emitted un-polarized photons.

45. The method of claim 34 further comprising the step of filtering the collected photons though an optical filter.

46. The method of claim 34 further comprising the step of spectrally separating the collected photons.

47. A system for obtaining a spatially accurate wavelength-resolved image of a sample, comprising:
    a photon emission source for illuminating the sample with a plurality of photons to thereby produce photons emitted by the sample;
    an optical lens for collecting the emitted photons;
    a filter for receiving the collected emitted photons and providing therefrom filtered photons; and
    a charged couple device for receiving the filtered photons and obtaining therefrom a spatially accurate wavelength-resolved image of the sample,
    wherein the illuminating photons do not pass through the optical lens, and
    wherein the emitted photons include plural sets of emitted photons,
    wherein each set of emitted photons contains photons in a predetermined wavelength band different from the predetermined wavelength band of the other sets of emitted photons, and
    wherein a spatially accurate wavelength-resolved image of the sample is obtained from each set of emitted photons.

48. The system of claim 47 wherein the wavelength-resolved image includes a Raman image.

49. The system of claim 47 wherein the wavelength-resolved image includes a luminescence emission image.

50. The system of claim 47 wherein the optical lens collects the emitted photons during a predetermined time interval.

51. The system of claim 50 wherein during said time interval the sample undergoes a change selected from the group of changes consisting of: spatial displacement, chemical interaction, chemical state, phase, growth, shrinkage, chemical decomposition, chemical metabolization, and physical strain.

52. The system of claim 47 wherein the photon emission source illuminates the sample with photons that travel at an angle that is oblique to a plane along which the sample is substantially oriented.

53. The method of claim 47 wherein the wavelength of the emitted photons is different than the wavelength of the illuminating photons.

54. The system of claim 47 wherein the photon emission source illuminates a side of the sample opposite the optical device.

55. The system of claim 47 wherein the photon emission source is an evanescence light source.

56. The system of claim 47 wherein the optical lens collects emitted polarized photons.

57. The system of claim 47 wherein the optical lens collects emitted un-polarized photons.

58. The system of claim 47 further comprising an optical filter.

59. The system of claim 47 wherein the filter spectrally separates the collected photons.

60. The system of claim 47 wherein the filter includes one or more of a photonic crystal, a mirror, a solid state optical device and a micromachined tunable filter.

61. The system of claim 47 wherein the filter is a tunable filter.

62. The system of claim 61 wherein the tunable filter is an optical filter.

63. The system of claim 47 further comprising a notch filter interposed between the optical lens and the filter.

64. The system of claim 47 wherein the photon illumination source is positioned at an angle with respect to an axis formed by the sample and the filter.

65. The system of claim 47 wherein the one or more wavelength-resolved images of a sample defines a Raman image.

66. The method of claim 1 wherein the step of illuminating the sample includes illuminating a side of the sample farthest from said optical device.

67. The system of claim 15 wherein the photon emission source illuminates a side of the sample farthest from said optical lens.

68. The method of claim 34 wherein the step of illuminating the sample with a plurality of photons further comprises illuminating a side of the sample farthest away from the optical device.

69. The system of claim 47 wherein the sample is interposed between the photon emission source and the optical lens.

* * * * *